United States Patent [19]

Holtkamp, Sr.

[11] Patent Number: Plant 6,428

[45] Date of Patent: Nov. 29, 1988

[54] AFRICAN VIOLET PLANT NAMED MEMPHIS

[76] Inventor: Reinhold Holtkamp, Sr., Werther Strasse 112, D4294 Isselburg, Fed. Rep. of Germany

[21] Appl. No.: 21,733

[22] Filed: Mar. 4, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet named Memphis, characterized by its single light pink, wavy flowers, girl-type leaves, strong, upright flower stems that curve toward the center to form a bouquet above the leaves, profuse flowering, vigorous growth habit, flowering 9–10 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Memphis.

The new cultivar was referred to during the breeding and selection process by the designation H 78/2, and is a product of a planned breeding program. The new cultivar was originated from a cross made by me in the controlled breeding program in Isselburg, Federal Republic of Germany. The female, or seed parent was a cultivar designated 69 Red Single. The male, or pollen parent was a cultivar designated E 148/1 Rose Star.

Memphis was discovered and selected by me in 1982 as a flowering plant within the progeny of the stated cross in a controlled environment in Haffen, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Memphis has not been observed under all possible environmental conditions. The phenotype may vary significantly with variations in environment such as temperature, light intensity and day length. The following observations, measurements and values describe the new cultivar as grown in Haffen, Federal Republic of Germany and Nashville, Tenn. under greenhouse conditions which closely approximate those generally used in commercial practice.

The following traits have been repeatedly observed and are determined to be basic characteristics of Memphis which in combination distinguish this African violet as a new and distinct cultivar:

(1) Strong upright flower stems curving toward the center.

(2) Long-lasting, non-dropping, single light pink, wavy flowers.

(3) Profuse flowering.

(4) Each plant carries 7–9 and more upright flower stems, each of which carries 10–14 flowers.

(5) Vigorous grower.

(6) Plant saleable 9 to 10 weeks after potting.

(7) Seed capsules push slightly through.

(8) Very attractive girl-type leaf, strongly serrated with a white to light green center that radiates along the veins.

(9) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (RHS), except where general colors of ordinary significance are referred to. Color values were taken under natural sunlight at approximately 2:00 p.m. in Nashville, Tenn.

Botanical classification: *Saintpaulia ionantha,* Ramat., cv. Memphis.

Parentage:

*Male parent.*—E 148/1 Rose Star.

*Female parent.*—69 Red Single.

Propagation: The new cultivar holds its distinguishing characteristics through successive propagations by leaf cuttings.

Plant: From 9 cm to 10 cm tall when grown in pots, and approximately 18–20 cm in diameter when fully grown.

*Leaves.*—General form: round, girl-type, curled up at the center. Diameter: 60–70 mm. Texture: velvety, shiny. Aspect: slightly indentated (especially the younger leaves), strongly serrated, slightly hairy, bright light green center radiating along the veins. Veins: upperside: well visible, light green towards the center; underside: very well pronounced, very light green, shiny, slight purplish touch in between the veins. Color (upper side): green group 137C; center of leaf bright green. Color (under side): green group 148D. Petiole: strong, upright, very light green, with purplish touch occasionally, hairy.

*Flowers.*—Buds: bell-shaped 6–8 mm just before opening, pinkish green. Sepals: Five (5). Color: purplish brown. Calyx: funnel-shaped. Peduncle: Character: hairy crest. Color: purplish brown. Individual flowers: Size: 40–45 mm. Shape: single, violet shaped, 3 large and 2 small petals; the difference in size becomes very pronounced on mature flowers. Color (upper side): 68 A–C, center somewhat darker. Color (under side): 65 B. Borne: each flower stem carries 10–14 flowers on a relatively thin peduncle that curves toward the center and is above the leaves. Flowering habit: Flowers 9–10 weeks after potting, producing a compact flower head. Under cooler growing conditions and more intensive lighting, the pink flower color is more intense.

*Reproductive organs.*—Stamens: 2. Anthers: 2 composed of 4 cells. Filaments: yellowish green, 4 mm. Pollen Color: yellow. Styles: 6 mm, pinkish, with a light green, hairy base of ovary.

*Roots.*—Normally developed, white when young turning slightly brownish when older.

Disease resistance: Good.

General observations: Memphis has a very attractive appearance due to its medium green strongly serrated leaves with a light green center, and its tight bouquet of light pink, wavy flowers that form a tight bouquet above the leaves. In the center of the flowers the pink color is darker and radiates into the middle of the petals, giving the flowers almost a star-shaped look. The flowers are long-lasting and non-dropping. Memphis has the characteristics of a semperflorence.

I claim:

1. A new and distinct cultivar of African violet named Memphis, as described and illustrated, and particularly characterized by its single light pink, wavy flowers, girl-type leaves, strong, upright flower stems that curve toward the center to form a bouquet above the leaves, profuse flowering, vigorous growth habit, flowering 9–10 weeks after potting, and its long-lasting and non-dropping flowers.

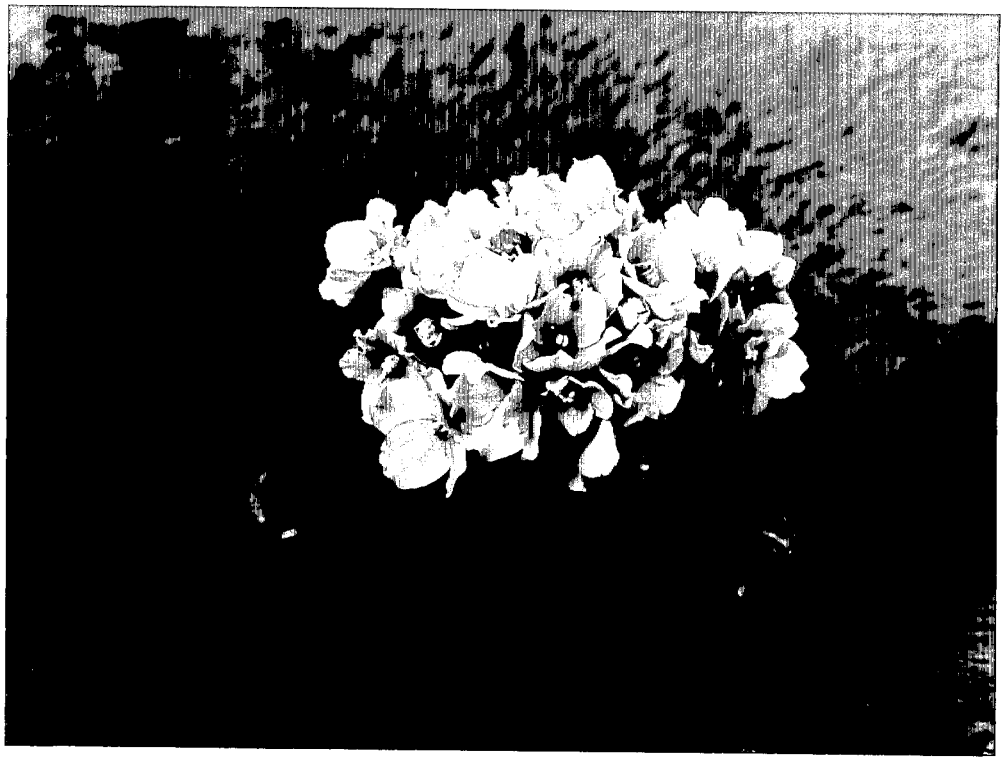

* * * * *